United States Patent [19]

Yamauchi et al.

[11] 4,384,852
[45] May 24, 1983

[54] DENTAL ROOT CANAL-TREATING APPLIANCE

[75] Inventors: Motonori Yamauchi, Yokosuka; Fumio Tanaka, Kawasaki; Churyo Suzuki, Ichikawa, all of Japan

[73] Assignees: Showa Yakuhin Kako Co., Ltd.; Tokyo Boshi Kabushiki Kaisha, both of Japan

[21] Appl. No.: 338,212

[22] Filed: Jan. 11, 1982

[30] Foreign Application Priority Data

Jan. 16, 1981 [JP] Japan .................................. 56-4831

[51] Int. Cl.³ ............................................. A61C 5/02
[52] U.S. Cl. ........................................ 433/81; 433/91
[58] Field of Search ............................ 433/81, 91, 96

[56] References Cited

U.S. PATENT DOCUMENTS

D. 247,574 3/1978 Orsing .................................... 433/91
1,189,735 7/1916 Quintin .................................. 433/91

Primary Examiner—Robert Peshock
Attorney, Agent, or Firm—Jacobs & Jacobs

[57] ABSTRACT

Dental root canal-treating appliance usable for cleaning pulp cavity and/or for application of medicine in the treatment of the root canal, the appliance being in the form of a slender rod of the diameter larger than 0.3 mm and of the length about 30 mm with appropriate numbers of continuous slits or conduits for absorption of liquid and/or blood in the canal and/or for retention of the medicine, at least one end of the rod, over the length less than about 2 mm from the tip, a thinner end section of the diameter about 0.25 mm being formed so that a shoulder is formed, the shoulder acts as an engagement-edge or stop-edge against the bottom of the canal and apical foramen in the diseased teeth.

6 Claims, 11 Drawing Figures

FIG. 10
FIG. 11
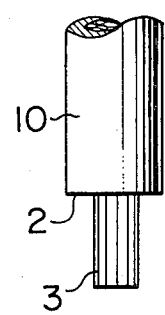
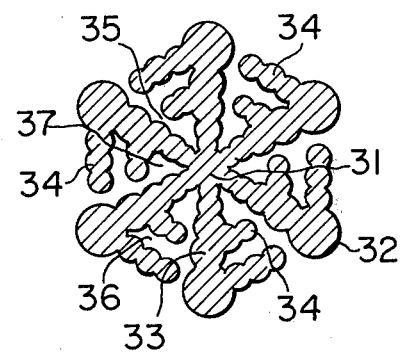

DENTAL ROOT CANAL-TREATING APPLIANCE

BACKGROUND OF THE INVENTION

When a dental pulp is deeply infected being provoked by dental caries, a treatment comprising pulling our the pulp (extirpation of the pulp) under anesthesia and filling the cavity (hereinafter referred to as pulp cavity) utlimately with cement to preserve and function the natural tooth within the oral cavity is required. In the treatment, a dental root canal-treating appliance for cleaning pulp cavity and/or for application of medicine is used.

The first stage of the treatment of root canal aims at killing innumerable bacteria on the wall surfaces of the root canal and in the dentine around the root canal wall and curing inflammation in periapical tissues. For this purpose, the dentist grates out the enamel layer 16 of the crown 15 of the diseased tooth (in the example shown in the attached illustration, an anterior tooth) (FIG. 1) and the wall of pulp chamber 17, then pulls out the dental pulp (nerve fibre and others) and grates out the root canal wall with an appliance, thus enlarges and forms the root canal 19 as shown in FIG. 2, leaving the apical foramen (hereinafter referred to as root canal formation). And thereafter an aqueous hydrogen peroxide, a solution of sodium hypochlorite, and water is poured into said root canal 19, or further thereafter, a disinfectant essentially comprising phenol, cresol, formaline etc. is applied thereto and the process is observed for several days. Thereby the infected root canal where bleeding, pus, serous and the like 21 (FIG. 3) were observed at first at the bottom of the root canal is made to gain momentum for curing. And subsequently, after confirming through culture test that the inside of the root canal is brought to aseptic state, zinc white-eugenol cement (as a favorable example, there is "CANALS", the trade mark of a product of Showa Yakuhin Kako K.K.) is filled and hardened, then in the pulp chamber 17, i.e. the root canal 19, zinc phosphate cement (as a favorable example, there is "Duraphos-S", the trade mark of a product of Showa Yakuhin Kako K.K.) is filled and hardened, and ultimately it is covered with gold crown (prothesis) to complete the treatment. And in such treating procedure in the prior art, for cleaning the inside of the root canal or for application of medicine, a cotton- or Japanese paper-work such as "broach cotton" formed by winding up a piece of cotton on to a wire, or "paper point" made by twisting a piece of Japanese paper has conventionally been used.

However, said "broach cotton" which the dentist produces by winding cotton onto a wire with his finger tips requires a skill to form it, and the amount of cotton cannot be definite, and if the cotton is used too much, it makes it difficult to insert it into the root canal, and if it is too small on the contrary, it not only cannot absorb the filth thoroughly, but since it is winded with finger tips, besmearing with bacteria cannot be avoided, and further it has the defect that cotton fibers remain in the canal. Said "paper point", on the other hand, has not so much defect as said "broach cotton", but it lacks firmness, and particularly when wetted, it often cannot reach the point around the apical foramen, and further, it takes a long time for absorbing not only pus but even water, and for absorbing blood, pus, serous or water from one root canal, it requires to use about 10 pieces of broach cotton or paper points in average.

On the other hand, as shown in FIG. 5 of the accompanying drawings, Japanese Utility Model Public Disclosure No. 93298/1979 proposes a root canal-treating appliance 10a as the product that improves the aforementioned defects, where one or both ends of a axially-arranged fibrous thin rod are formed into a conical shape and sterilized. The major improvement of this improved product lies in that the fibrous material is even up to the axial direction, but when a fibrous material even up to the axial direction is merely formed into the needlelike taper 10a and used for the treatment, the fiber ends, i.e. fine splits are projecting which not only impart extra irritation to the periapical tissue but also injure even the periodontal membrane, and quite naturally push out bacteria outside the apical foramen and may invite aggravation of the disease. Since the wall surface of the root canal formation 19, i.e. root canal wall 20, is composed of dentine but has tubles, it is apt to get injured by the needle-like taper having fine splits. Furthermore, because all the peripheral surface of the taper 10a having the length 20-30 mm has to be ground with a grinder or the like, the surface of the appliance itself lacks in smoothness, and moreover, the ground powder of the fibrous material is apt to attach and may remain within the root canal as foreign matters. Furthermore, with the structure of such shape, it is difficult to gain a definite drift of the liquid absorption within the root canal, and due to the irregular absorption from the surrounding surfaces, absorption from the tip end tends to be disturbed. And because of these defects, further improvements have been called for the appliance to be used for depuration and medicine-application for the inside of the root canal including the apical foramen 13.

BRIEF DESCRIPTION OF THE DRAWING

FIG. 10 shows another embodiment of the rod of the present invention having shoulder forming almost right angle; and FIG. 11 shows another example of the enlarged cross-section of the root canal-treating appliance of the present invention.

DESCRIPTION OF THE INVENTION

The object of the present invention is to provide an improved appliance used in the treatment of the root canal.

According to the structure of the invention of the present application, all defects of the conventional arts can be eliminated, and improvement in treating effects can satisfactorily be anticipated therewith.

Figure 1:
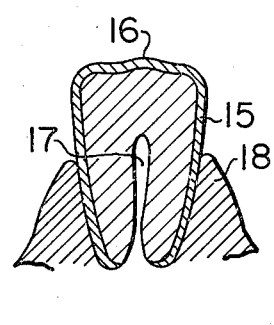
FIG. 1 of the attached drawing shows a diseased tooth (an anterior tooth)
Figure 2:
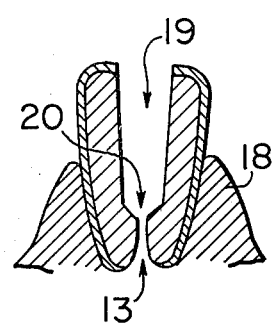
FIG. 2 shows a root canal formed by grinding off the wall of the pulp chamber.
Figure 3:
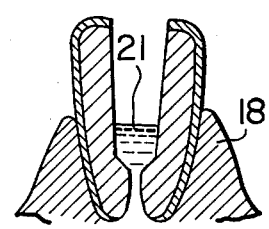
FIG. 3, a bottom of the root canal with blood, pus, serous retained therein.
Figure 4:
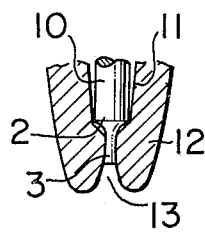
FIG. 4 illustrates the condition where the root canal-treating appliance of the present invention is inserted in the root canal.
Figure 5:
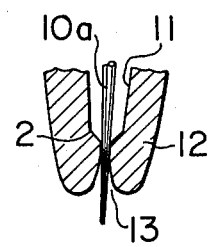
FIG. 5 shows the condition where a conventional root canal-treating appliance of the prior art is inserted in the root canal.
Figure 6:
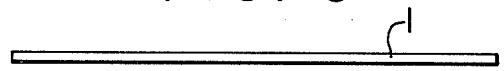
FIG. 6 shows the thin rod body (before the smaller diameter section is formed)
Figure 7:
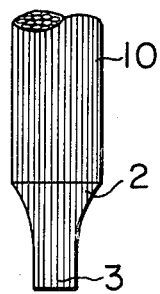
FIG. 7 shows one example of the root canal-treating appliance (after the smaller diameter section was formed) comprising the thin rod body of the present invention.
Figure 8:
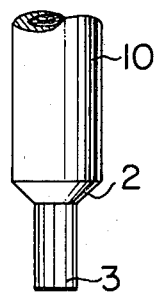
FIG. 8 shows another example of the root canal-treating appliance of the present invention (slightly different in shape of the shoulder section from that of FIG. 7)

Explaining further in detail, the structure of the appliance of the invention of the present application is formed by: forming a thin rod body 1 of the length about 30 mm by cutting a monofilamental shaped article comprising a high molecular material, with appropriate numbers of continuous slits, and having a diameter larger than 0.3 mm, as shown in FIG. 6, then subjecting at least one end of the thin rod, over the length less than about 2 mm from the tip, to grinding to form a thinner end section 3 of the diameter about 0.25 mm and at the same time to form a shoulder section 2 as shown in FIGS. 7 and 8, then subjecting it to sterilization by means of ethylene oxide or X-ray or the like to obtain a dental canal-treating appliance 10 for depuration and/or medicine application. Now that the appliance of the invention of the present application has the structure such as explained above, the shoulder section 2 of the appliance is formed as an engagement-edge or stop-edge against the upper section 12 of the apical foramen 13, i.e. the bottom 20 of the root canal 19, in inserting it into the root canal as shown in FIG. 4. That is to say, the word "engagement-edge" or "stop-edge" is used relating to the shoulder 2 in the sense that the end of the appliance is prevented from being inserted too deep and running too far piercing into the apical foramen. Thus, according to the present invention, the thinner end section 3 that serves as the absorbing end cannot break into or penetrate the apical foramen.

The language "engagement-edge" or "stop-edge" means the outer peripheral edge of annular shoulder 2 (FIG. 10) on the forward end portion of the slender rod 10 (FIG. 10) which edge coincides with the inner peripheral edge of the annular shoulder on the inner periphery of the lower part of root canal 19. The slender rod (FIG. 10) is also within the range of the claim of the present application and will give the rod having sloping or tapered shape (FIG. 7 or FIG. 8) when the annular edge 2 of the rod (FIG. 10) being grounded.

Since only the section to be inserted into the apical foramen is formed to have a smaller diameter, the appliance can be formed accurately in high precision in its outer diameter, position of the shoulder, shape of the smaller diameter section, thickness and the shape at the end of the smaller diameter section, in broad ranges and at the same time the attaching and remaining matters produced by grinding can be reduced. And also, since the dental appliances are used for root canal formed by such as reamers (e.g. drills equipped with a reamer) or files (appliances for removing nerve fiber) of which outer diameters are known and standardized, it is possible to unify the diameters of the appliance of the present invention with the standards of such dental appliances. In this matter, even in case of a curved root canal, the apical foramen can accurately be explored. Accordingly, depuration of the apical foramen and medicine application thereto where blood, pus and serous 21 are most apt to reside and washing is quite difficult can readily be practised. Furthermore, since the end of the smaller diameter section 3 is formed into the shape which can readily be contacted directly with liquid within the root canal 19 (particularly at its bottom 20), absorption from the bottom end of the spical foramen is improved and steady.

Figure 9:
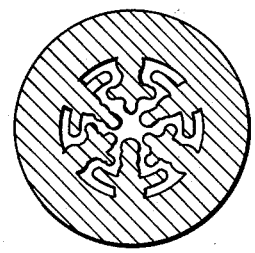
FIG. 9 shows one example of the enlarged cross-section of the root canal-treating appliance of the present invention.

The structure of the appropriate numbers of continuous conduit formed in the thin rod body, that is the factor that specifies the absorbing function, can readily obtained in many variant capillary structures such as multiple perforated holes, channels and slits, or porous cells, or such shapes as shown in FIG. 9 where plurality of projecting parts are formed from the inner surface of the rod body toward the center thereof, or porous filamentary shapes, etc. by combination of the type of the high molecular materials and the shape thereof with the known method for forming such rod. Therefore, the appliances variant in their liquid-absorbing characteristic can readily and economically be provided. As a favorable example of the material and method for manufacture, the appliance of the invention of the present application can be readily produced by application of, for example, the method for manufacture of pen-shaped articles employed in the technical field of producing writing appliances where liquid is absorbed by capillary action and then discharged. Particularly there are such methods that are applicable for the manufacture of the appliance of the present invention as the method for manufacturing pen-shaped articles in which a continuous, monofilamentary shaped body having a foreign shaped cross-section is formed by melting and extrusion-molding a thermoplastic synthetic polymer material such as synthetic resins of polyolefin, polyamide, polyurethane, polyacetal or cellulose type; or the method for manufacturing pen-shaped articles wherein a porous and fibrous continuous monofilamentary shaped body is formed by adhering and bonding a fiber bundle material of semi-synthetic or synthetic polymer fibers, such as acetyl cellulose, polyacrylonitrile, polyethylene terephthalate, polyamide, polypropylene, etc., or a composite fiber material obtained by combination of these polymer materials, such as polyethylene terephthalate and polyamide, subjected to crimping treatment.

The rod indicated in FIG. 9 has a shape in which plurality of projections are formed from the inner wall of a hollow tube to the direction of the center of the tube and hence the rod possesses outer closed surface. On the contrary, the rod having open outer side (FIG. 11) is also within the scope of the present invention. Such a type of rod is composed of a fine rod body or a continuous monofilament bar 31 (FIG. 11) made of such as high molecular material having plurality of brunched projections 32, 33 and 34 which form plurality of slots or compartment conduits 35, 36 and 37 (FIG. 11), said conduits absorb liquid 21 in the root canal 19 by capillary action.

The root canal-treating appliance of the invention of the present application is formed by forming a shoulder section 2 and a smaller diameter end section 3 at one end of a thin rod body 1 having continuous fine slits, comprising a polymer material or a composite fibers, then subjecting it to sterilization, therefore, it facilitates accurate exploring, measuring, cleaning of the inside of root canal, and medicine application and the like, and at the same time it promotes the improvement of the effects of dental treatment.

We claim:

1. A dental root canal-treating appliance which comprises a body of a high molecular weight material in the form of a thin rod having in the inside thereof, from one end to the other, a plurality of continuous fine slits or conduits operable to absorb liquid by capillary action, at least one end of said rod having a reduced diameter, the portion between said thin rod and said end section of reduced diameter forming a shoulder section, said shoulder section being operable as an engagement-edge or stop-edge against the bottom of the root canal and apical foramen in the diseased tooth.

2. A dental root canal-treating applicance as described in claim 1, wherein said thin rod is made of fiber bundle materials or composite fiber materials.

3. A dental root canal-treating appliance as described in claim 2, wherein the surface of the appliance is smooth and free of projecting fiber ends.

4. A dental root canal-treating appliance as described in claim 1, wherein said appliance comprises a thin rod body made of a high molecular weight material or synthetic resin, whose cross-section has a shape having a plurality of parts projecting from the inner surface of said rod toward the center thereof.

5. A dental root canal-treating appliance as described in claim 1, wherein said appliance comprises a thin rod body having an outer diameter less than about 0.5 mm, an outer diameter at the reduced section of about 0.25 mm, and a length of about 20–30 mm.

6. A dental root canal-treating appliance as described in claim 1 which comprises a thin continuous monofilament bar or fine rod body of a high molecular material or synthetic resin, whose cross-section has a shape having plurality of branched projections from the central part thereof outwardly and laterally so as to form plurality of compartment conduits.

* * * * *